(12) United States Patent
Carlson et al.

(10) Patent No.: US 11,111,513 B2
(45) Date of Patent: Sep. 7, 2021

(54) METHODS OF REMOVING ONE OR MORE COMPOUNDS FROM A LIGNOCELLULOSIC HYDROLYSATE VIA GAS STRIPPING, AND RELATED SYSTEMS

(71) Applicant: POET Research, Inc., Sioux Falls, SD (US)

(72) Inventors: David Charles Carlson, Brandon, SD (US); Benjamin M. Gerdes, Yankton, SD (US); Casey C. Jenks, Ethan, SD (US); Ryan J. Bouza, Harrisburg, SD (US); Cory James Sarks, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 102 days.

(21) Appl. No.: 16/302,864

(22) PCT Filed: May 18, 2017

(86) PCT No.: PCT/US2017/033241
§ 371 (c)(1),
(2) Date: Nov. 19, 2018

(87) PCT Pub. No.: WO2017/201233
PCT Pub. Date: Nov. 23, 2017

(65) Prior Publication Data
US 2019/0292573 A1 Sep. 26, 2019

Related U.S. Application Data

(60) Provisional application No. 62/339,600, filed on May 20, 2016.

(51) Int. Cl.
| | |
|---|---|
| *C07D 307/50* | (2006.01) |
| *C08H 8/00* | (2010.01) |
| *C12P 7/10* | (2006.01) |
| *C12P 17/04* | (2006.01) |
| *C12P 19/02* | (2006.01) |
| *C12P 19/14* | (2006.01) |

(52) U.S. Cl.
CPC ............ *C12P 19/02* (2013.01); *C07D 307/50* (2013.01); *C08H 8/00* (2013.01); *C12P 7/10* (2013.01); *C12P 17/04* (2013.01); *C12P 19/14* (2013.01); *C12P 2201/00* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 8,450,094 B1 | 5/2013 | Narendranath et al. | |
| 9,034,631 B2 | 5/2015 | Narendranath et al. | |
| 9,068,206 B1 | 6/2015 | Kwiatkowski et al. | |
| 9,278,379 B2 | 3/2016 | Carlson et al. | |
| 9,340,767 B2 | 5/2016 | Narendranath | |
| 9,469,859 B1 | 10/2016 | Bly et al. | |
| 10,113,187 B2 | 10/2018 | Bushong et al. | |
| 2009/0098617 A1 | 4/2009 | Burke et al. | |
| 2014/0024826 A1 | 1/2014 | Narendranath et al. | |
| 2015/0203885 A1 | 7/2015 | Noordam | |
| 2015/0368679 A1 | 12/2015 | Narendranath et al. | |
| 2018/0171285 A1 | 6/2018 | Narendranath et al. | |
| 2018/0273988 A1 | 9/2018 | Lewis et al. | |

FOREIGN PATENT DOCUMENTS

| | | | |
|---|---|---|---|
| CN | 101942529 A | 1/2011 | |
| WO | 2009046538 A1 | 4/2009 | |
| WO | 2011070602 A1 | 6/2011 | |
| WO | 2012103281 A1 | 8/2012 | |
| WO | 2012125739 A1 | 9/2012 | |
| WO | 2014072390 A1 | 5/2014 | |
| WO | 2014072393 A1 | 5/2014 | |
| WO | 2014072395 A1 | 5/2014 | |
| WO | 2014176531 A2 | 10/2014 | |
| WO | 2015075277 A1 | 5/2015 | |
| WO | 2015165951 A1 | 11/2015 | |
| WO | 2015165952 A1 | 11/2015 | |
| WO | WO-2015165951 A1 * | 11/2015 | ............... D21C 3/26 |
| WO | 2016096971 A1 | 6/2016 | |
| WO | 2016201031 A1 | 12/2016 | |
| WO | 2017091361 A1 | 6/2017 | |
| WO | 2017218380 A1 | 12/2017 | |
| WO | 2018185071 A1 | 10/2018 | |

OTHER PUBLICATIONS

Hu et al., Scientific Reports, vol. 5, No. 9428, pp. 1-9; Mar. 30, 2015 (of record). (Year: 2015).*
Hu et al., Scientific Reports, vol. 5, No. 9428, pp. 1-9; electronically available Mar. 30, 2015 (of record). (Year: 2015).*
International Search Report for International Application No. PCT/US2017/033241, dated Aug. 16, 2017 (3 pages).
Buijtenen et al., "Furfural Production by 'Acidic Steam Stripping' of Lignocellulose", ChemSusChem, pp. 2132-2136, 2013, (6 pages).
Hu et al., "A Novel Method for Furfural Recovery Via Gas Stripping Assisted Vapor Permeation by a Polydimethylsiloxane Membrane", Scientific Reports, pp. 1-9, Mar. 30, 2013, (9 pages).
Anish et al., "Bioethanol from Lignocellulosic Biomass", Part III Hydrolysis and Fermentation, pp. 159-173, (8 pages).
Canilha et al., "Bioconversion of Sugarcane Biomass into Ethanol: An Overview about Composition, Pretreatment Methods, Detoxification of Hydrolysates, Enzymatic Saccharification, and Ethanol Fermentation", Journal of Biomedicine and Biotechnology, vol. 2012, Article ID 989572, (15 pages).

* cited by examiner

*Primary Examiner* — Soren Harward
*Assistant Examiner* — Paul D. Pyla
(74) *Attorney, Agent, or Firm* — Kagan Binder, PLLC (57) ABSTRACT

The present disclosure includes methods and systems for removing one or more fermentation inhibitors (e.g., furfural) from a hydrolysate composition (e.g., a whole broth hydrolysate) by gas stripping the one or more fermentation inhibitors from the hydrolysate composition.

14 Claims, 9 Drawing Sheets

FIG. 5
ACID HYDROLYSIS REACTOR, LIQUEFACTION REACTOR, SACCHARIFICATION REACTOR, OR PROPAGATION VESSEL

FIG. 6
COLUMN SEPARATE FROM ACID HYDROLYSIS, LIQUEFACTION REACTOR, SACCHARIFICATION REACTOR, AND PROPAGATION VESSEL
(MAY BE PACKED OR UNPACKED)

METHODS OF REMOVING ONE OR MORE COMPOUNDS FROM A LIGNOCELLULOSIC HYDROLYSATE VIA GAS STRIPPING, AND RELATED SYSTEMS

RELATED APPLICATIONS

The present application claims the benefit of commonly owned provisional Application having Ser. No. 62/339,600, filed on May 20, 2016, which provisional Application is incorporated herein by reference in its entirety.

FIELD

The present disclosure is related to removing one or more hydrolysis byproducts from lignocellulosic hydrolysate liquor. More particularly, the present disclosure is related to using gas stripping to remove one or more hydrolysis byproducts from a lignocellulosic hydrolysate.

BACKGROUND

Hydrolysis of lignocellulosic material can produce one or more byproducts. One or more of such byproducts can inhibit enzymatic activity of enzymes, growth of yeast and other microorganisms, and/or fermentation of monosaccharides to a biochemical. For example, acid hydrolysis of corn stover can produce one or more compounds that can inhibit enzymatic activity of cellulases and/or hemicellulases, growth of yeast and other microorganisms, and fermentation of monosaccharides to a biochemical such as ethanol. Examples of such compounds include acetic acid from ester hydrolysis of acetyl groups on xylan and lignin, phenolic compounds derived from lignin hydrolysis, and/or furfural and 5-hydroxymethylfurfural (HMF), which can be produced by the dehydration of pentoses and hexoses, respectively.

There is a continuing need to provide methods and systems to remove fermentation inhibitors such as furfural.

SUMMARY

In some embodiments of the present disclosure is a method of removing at least a portion of furfural from a hydrolysate composition, wherein the method includes:
a) providing a whole broth hydrolysate composition including:
 i) pentose;
 ii) furfural, wherein the furfural is present in a first concentration;
 iii) cellulose and/or hexose; and
 iv) lignin;
b) injecting a first volume of a gas into the whole broth hydrolysate composition to provide a treated, whole broth hydrolysate composition, wherein the treated, whole broth hydrolysate composition includes furfural in a second concentration, wherein the second concentration is less than the first concentration; and
c) recovering a second volume of the gas from the treated, whole broth hydrolysate composition, wherein the second volume of the gas comprises furfural.

In some embodiments of the present disclosure is a system for removing at least a portion of furfural from a whole broth hydrolysate composition. The system includes:
a) a source of a whole broth hydrolysate composition, wherein the whole broth hydrolysate composition comprises:
 i) pentose;
 ii) furfural, wherein the furfural is present in a first concentration;
 iii) cellulose and/or hexose; and
 iv) lignin;
b) a gas injection system in fluid communication with the source of the whole broth hydrolysate composition, wherein the gas injection system is configured to inject a volume of a gas component into the whole broth hydrolysate composition to provide a treated, whole broth hydrolysate composition, wherein the treated, whole broth hydrolysate composition comprises furfural in a second concentration, wherein the second concentration is less than the first concentration; and
c) a gas recovery system in fluid communication with the whole broth hydrolysate composition, wherein the gas recovery system is configured to recover a second volume of the gas from the whole broth hydrolysate composition, wherein the second volume of the gas comprises furfural.

In some embodiments of the present disclosure is a method of removing at least a portion of furfural from a hydrolysate composition, wherein the method includes:
a) contacting lignocellulosic biomass with an aqueous composition to hydrolyze hemicellulose present in the lignocellulosic biomass to fonn a hydrolysate composition, wherein the hydrolysate composition includes a pentose liquor comprising sulfuric acid and furfural, wherein the furfural is present in a first concentration;
b) injecting a volume of a gas component into the hydrolysate composition to provide a treated, hydrolysate composition, wherein the treated, hydrolysate composition comprises furfural in a second concentration, wherein the second concentration is less than the first concentration; and
c) recovering a second volume of the gas from the treated, hydrolysate composition, wherein the second volume of the gas includes furfural.

In some embodiments of the present disclosure is a system for removing at least a portion of furfural from a hydrolysate composition, wherein the system includes:
a) a hydrolysis system configured to provide a hydrolysate composition, wherein the hydrolysate composition includes a pentose liquor comprising sulfuric acid and furfural, wherein the furfural is present in a first concentration;
b) a gas injection system in fluid communication with hydrolysis system, wherein the gas injection system is configured to inject a volume of a gas component into the hydrolysate composition to provide a treated hydrolysate composition, wherein the treated hydrolysate composition includes furfural in a second concentration, wherein the second concentration is less than the first concentration; and
c) a gas recovery system in fluid communication with the hydrolysis system, wherein the gas recovery system is configured to recover a second volume of the gas from the hydrolysis system, wherein the second volume of the gas includes furfural.

DETAILED DESCRIPTION

Disclosed in embodiments herein are methods and systems for removing at least a portion of fermentation inhibitor such as furfural from a hydrolysate composition such as a whole broth hydrolysate composition.

A. Hydrolysate Composition

As used herein, a "hydrolysate" is derived from at least partial hydrolysis of polysaccharide in a biomass material into oligosaccharides and/or monosaccharides. For example, a polysaccharide such as cellulose can be hydrolyzed into six carbon sugars such as glucose and a polysaccharide such as hemicellulose can be hydrolyzed into five carbon sugars such as xylose.

Biomass includes, for example, lignocellulosic material such as corn cobs and corn stover (e.g., stalks and leaves) made available during or after harvesting of the corn kernels, fiber from the corn kernel, switchgrass, farm or agricultural residue, wood chips or other wood waste, and other plant matter (grown for processing into bioproducts or for other purposes). Lignocellulosic biomass includes hemicellulose, cellulose, and lignin.

A hydrolysate can be a "whole broth" hydrolysate or a fraction thereof. As used herein a whole broth hydrolysate composition refers to a product of biomass hydrolysis and includes a solid component and a liquid component. In some embodiments, the solid component can include solid, unhydrolyzed materials of a biomass feedstock such as lignin, cellulose, and/or hemicellulose. In some embodiments, the liquid component can be a liquid hydrolysate (or liquor) and can include water, sugar and byproducts of hydrolysis such as fermentation inhibitors. Examples of fermentation inhibitors include furfural, hydroxymethylfurfural (I-IMF), phenol compounds, mixtures thereof, and the like. In some embodiments, a whole broth hydrolysate includes at least pentose, furfural, cellulose and/or hexose, and lignin. A whole broth hydrolysate can have a total solids (dissolved and suspended solids) content in the range from 10 to 30 percent, from 12 to 25 percent, or even from 13 to 20 percent.

B. How to Make a Hydrolysate Composition

A hydrolysate composition can be made by hydrolyzing a lignocellulosic substrate to provide a solid component including glucan and lignin and a liquid component including a monosaccharide such as xylose and/or glucose.

Hydrolysis of polysaccharides in biomass can occur by a wide variety of techniques such as contacting the biomass with hot water, acid, base, enzyme(s), and the like.

Hydrolyzing lignocellulosic substrates to provide, e.g., xylose and/or glucose is described in, e.g., U.S. Pat. No. 5,424,417 (Torget et al.); U.S. Pat. No. 6,022,419 (Torget et al.); and U.S. Pat. No. 8,450,094 (Narendranath et al.), and U.S. Publication Number 2010/0233771 (McDonald et al.), wherein the entireties of said patent documents are incorporated herein by reference for all purposes.

Hydrolysis can create byproducts that can be inhibitory to downstream processes such as enzymatic saccharification of polysaccharide and/or oligosaccharide material and/or downstream fermentation of monosaccharides. Examples of such inhibitory byproducts from hydrolysis include acetic acid from ester hydrolysis of acetyl groups on xylan and lignin; phenolic compounds derived from lignin hydrolysis; and/or furfural and 5-hydroxymethylfurfural (HMF), which can be produced by the dehydration of pentoses and hexoses, respectively.

Hydrolysis of a lignocellulosic biomass is described herein below with reference to FIGS. 1-4 for illustration purposes.

Figure 1:
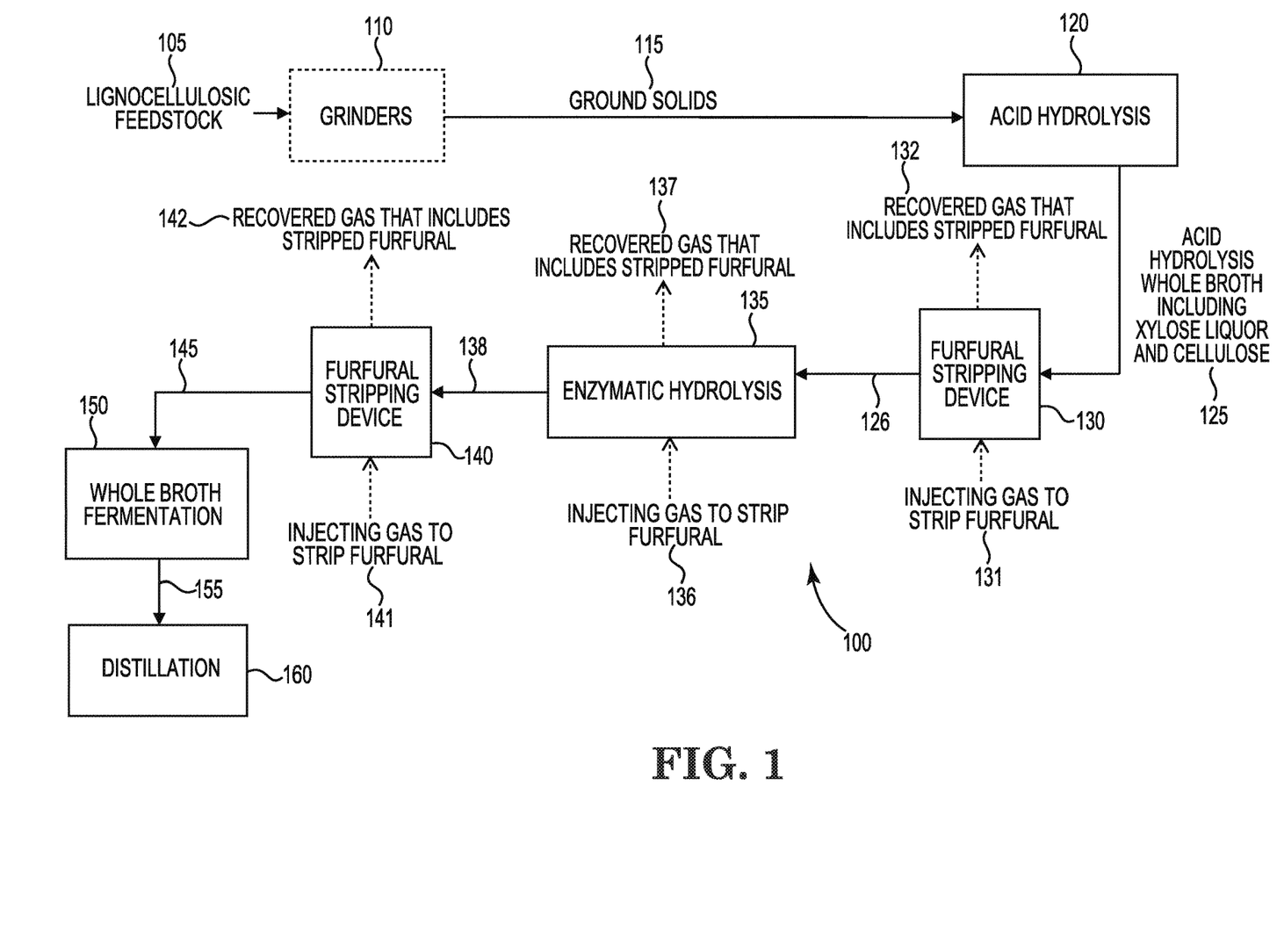
FIG. 1 shows a schematic of an exemplary process for gas stripping furfural from a whole broth hydrolysate in the context of a system 100 for making ethanol via fermentation.

Before hydrolysis, a lignocellulosic feedstock can be prepared by a variety of techniques such as size reduction, steaming, combinations of these, and the like. As shown in FIG. 1, lignocellulosic feedstock 105 can be prepared prior to hydrolysis such as by grinding the lignocellulosic feedstock in one or more grinders 110 into ground solids 115 to reduce the size of the feedstock and increase its surface area for contact with a hydrolysis medium.

B.1 Acid Hydrolysis

FIG. 1 shows an embodiment of hydrolyzing lignocellulosic feedstock by passing a whole broth hydrolysate from acid hydrolysis 120 to enzymatic hydrolysis 135.

As shown in FIG. 1, acid hydrolysis 120 can convert hemicellulose in the ground biomass 115 into one or more pentoses such as xylose. In some embodiments, the acid hydrolysis includes contacting lignocellulosic biomass with an aqueous composition to hydrolyze at least a portion of the hemicellulose into one or more oligosaccharides and/or one or more pentoses, and form a first whole broth hydrolysate composition including at least pentose, cellulose, lignin, and furfural. In some embodiments, acid hydrolysis hydrolyzes at least a portion of cellulose into glucose.

During acid hydrolysis, the "severity" can be adjusted by varying one or more of time period, temperature, and pH of hydrolysis. In some embodiments, during hydrolysis an aqueous composition can have a pH in the range from 1 to 5, or even 2 to 3. The aqueous composition can include an acid such as sulfuric acid present in a concentration in the range from 0.2 to 1.3% w/w, or even 0.5 to 1% w/w. In some embodiments, acid hydrolysis can be performed for a time period in a range from 15 minutes to 5 hours, or even 30 minutes to 4 hours. In some embodiments, acid hydrolysis can be performed at a temperature in the range from greater than 100° C. to 170° C., or even from 110° C. to 150° C.

Acid hydrolysis can be performed in a variety of system and apparatus configurations. In some embodiments, an acid hydrolysis system can include a first reactor system in fluid communication with a source of lignocellulosic biomass and a source of an aqueous composition. The first reactor system can include at least one reactor configured to contact the lignocellulosic biomass with the aqueous composition to hydrolyze at least a portion of the hemicellulose into one or more oligosaccharides and/or one or more pentoses, and form a first, whole broth hydrolysate composition including at least pentose, cellulose, lignin, and furfural.

B.2 Optional Steam Explosion

Figure 2:
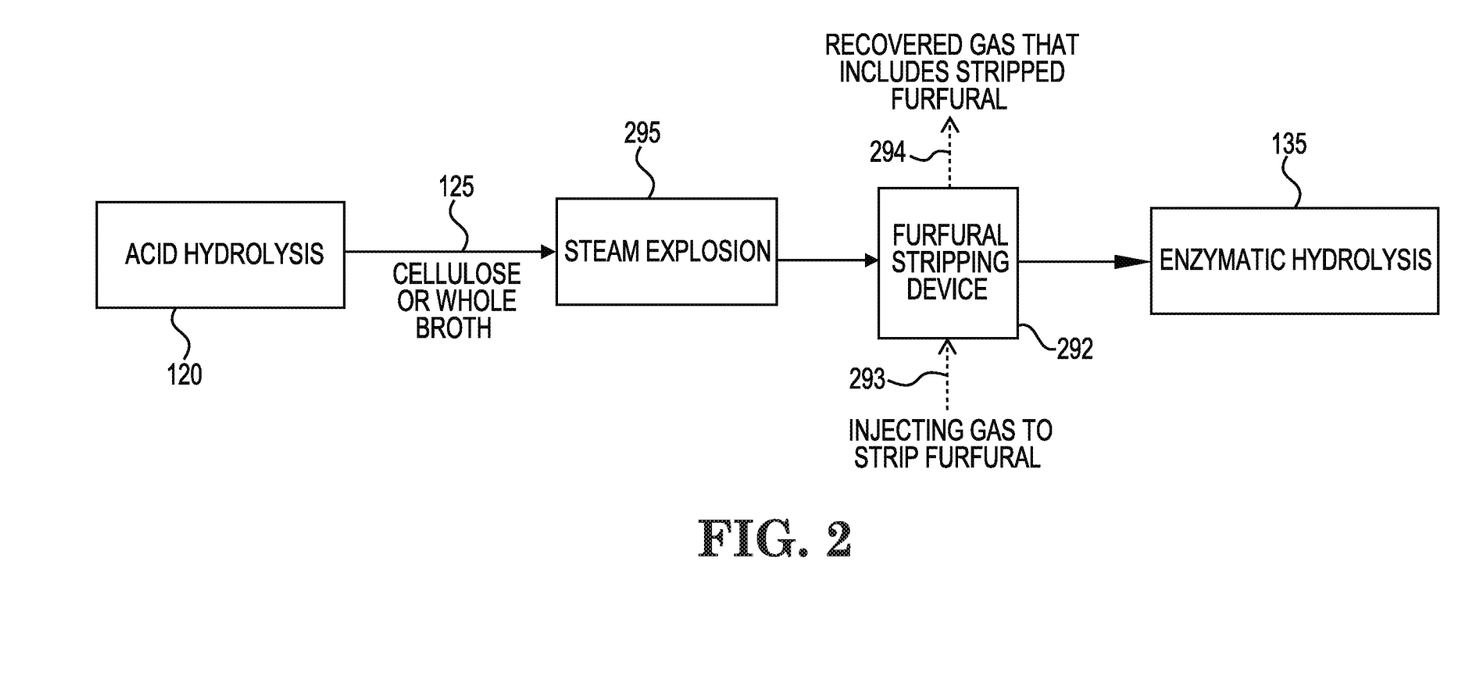
FIG. 2 shows a schematic of an exemplary, optional steam explosion process that can be included in the process of FIG. 1.

Optionally, as shown in FIG. 2, the whole broth hydrolysate 125 from acid hydrolysis 120 can be subjected to steam explosion 295 conditions that make the cellulose in the whole broth hydrolysate 125 more accessible during enzymatic hydrolysis 135. In some embodiments, steam explosion also forms furfural. Steam explosion 295 can be performed in a system that includes at least one reactor configured to receive the hydrolysate composition 290 and subject the cellulose in the hydrolysate composition 290 to a steam explosion process under conditions that form a steam-exploded, hydrolysate composition including at least cellulose, lignin, and furfural.

During steam explosion, cellulose (either in a whole broth hydrolysate or hydrolysate with a portion of xylose liquor removed) can be subjected to a relatively elevated pressure and temperature so that moisture impregnated within the cellulose network is in a liquid state. Then, the pressure can be reduced so that the liquid "flashes" to a gas state so that the sudden expansion with the cellulose network causes at least a portion of the cellulose structure to rupture, thereby increasing the surface area of the cellulose for increased exposure to cellulase enzymes. In some embodiments, the superheated hydrolysate composition can be flashed to a reduced pressure by continuously discharging the composition through an orifice. In some embodiments, a hydrolysate composition including cellulose can be subjected to a temperature in the range from 320° F. to 400° F. and a pressure in the range from 75 psig to 235 psig, followed by suddenly exposing the hydrolysate composition to a reducing pressure such as atmospheric pressure. In some embodiments, a hydrolysate composition including cellulose can be subjected to a temperature in the range from 350° F. to 385° F. and a pressure in the range from 120 psig to 195 psig, followed by suddenly exposing the hydrolysate composition to a reducing pressure such as atmospheric pressure.

After steam explosion 295, a fermentation inhibitor such as furfural can be stripped from the steam-exploded hydrolysate using a furfural stripping device 292 to inject a gas 293 into the hydrolysate and recover a gas 294 that includes at least a portion of the stripped furfural. Gas stripping of furfural is further discussed in section D below.

Figure 3:
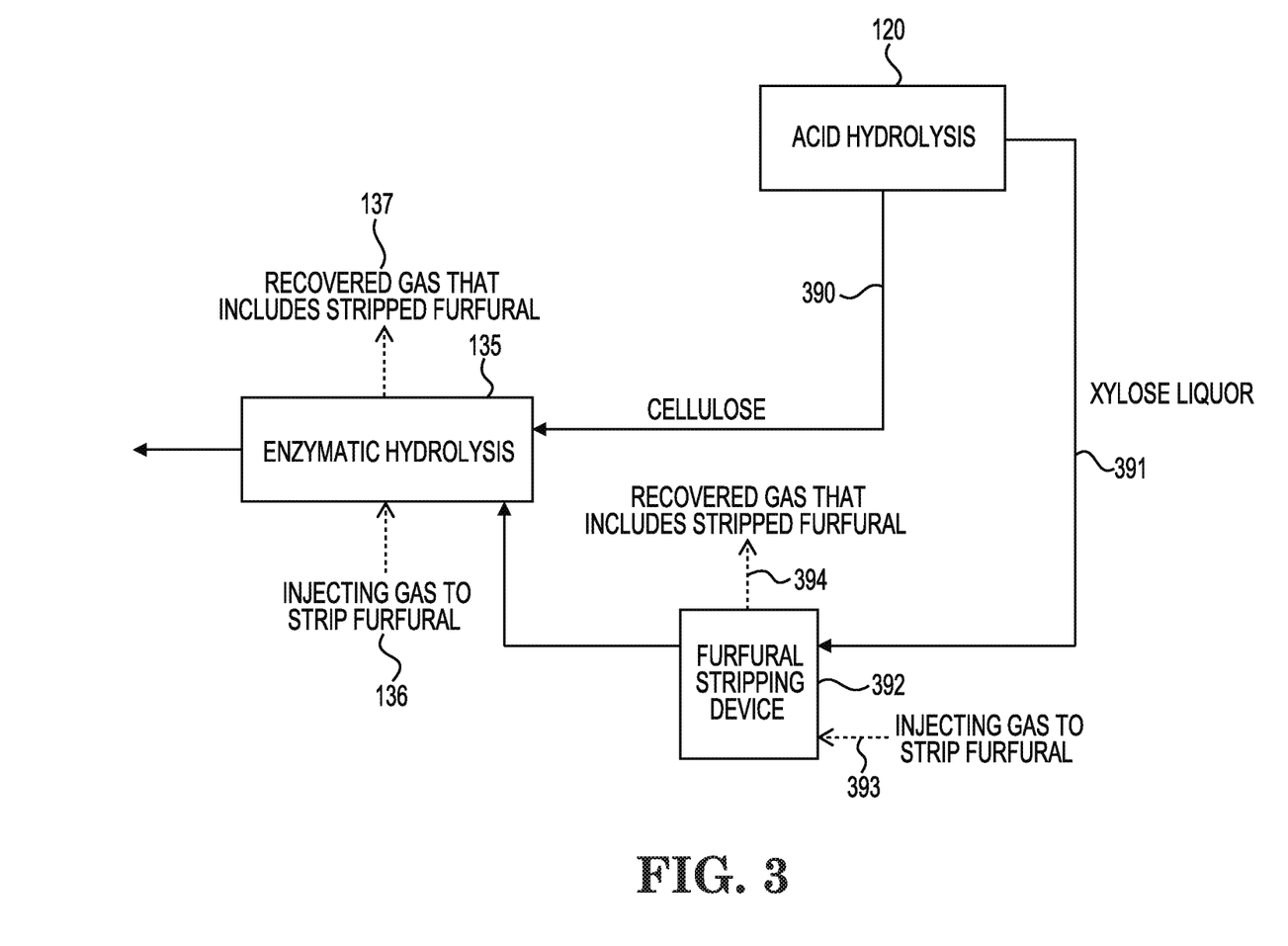
FIG. 3 shows a schematic of an exemplary, alternative process that can be used between the acid hydrolysis and enzymatic hydrolysis shown in FIG. 1.

Alternatively, as shown in FIG. 3, the whole broth hydrolysate from acid hydrolysis 120 can be separated prior to steam explosion into a xylose liquor stream 391 and a solid component stream 390 including at least cellulose and lignin. The xylose liquor can be separated from the solid component after hydrolysis via one or more of centrifugation, filtering, etc. The solid component stream 390 can be subjected to steam explosion 295 conditions to make the cellulose in the solid component stream 390 more accessible during enzymatic hydrolysis 135. Advantageously, by separating at least a portion of the xylose from the cellulose into a liquor stream 391, the xylose in the liquor stream 391 can avoid steam explosion condition so that such xylose is not converted to furfural. Nonetheless, steam explosion of the cellulose in the solid component stream 390 can still create furfural due a residual amount of xylose that may remain in solid component stream 390.

In the embodiment shown in FIGS. 2 and 3, steam explosion 295 can be performed in a steam explosion system that is in fluid communication with a separation system (not shown). The separation system can be coupled to the acid hydrolysis system 120 to separate the whole broth hydrolysate into the xylose liquor stream 391 and the solid component stream 390. After steam explosion, the solid component stream 390 and the xylose liquor stream can be recombined and subjected to enzymatic hydrolysis 135.

B.3 Enzymatic Hydrolysis

As shown in FIGS. 1 and 2, after acid hydrolysis 120 and optional steam explosion 295, at least a portion of the cellulose in the hydrolysate composition can be enzymatically hydrolyzed 135 to hydrolyze the cellulose in into glucose. In some embodiments, as shown in FIG. 1, at least a portion of the cellulose in the first whole broth hydrolysate composition 125 provided directly from acid hydrolysis 120 can be enzymatically hydrolyzed 135 to form a second whole broth hydrolysate composition 138 that includes at least pentose, glucose, lignin, and furfural.

Figure 4:
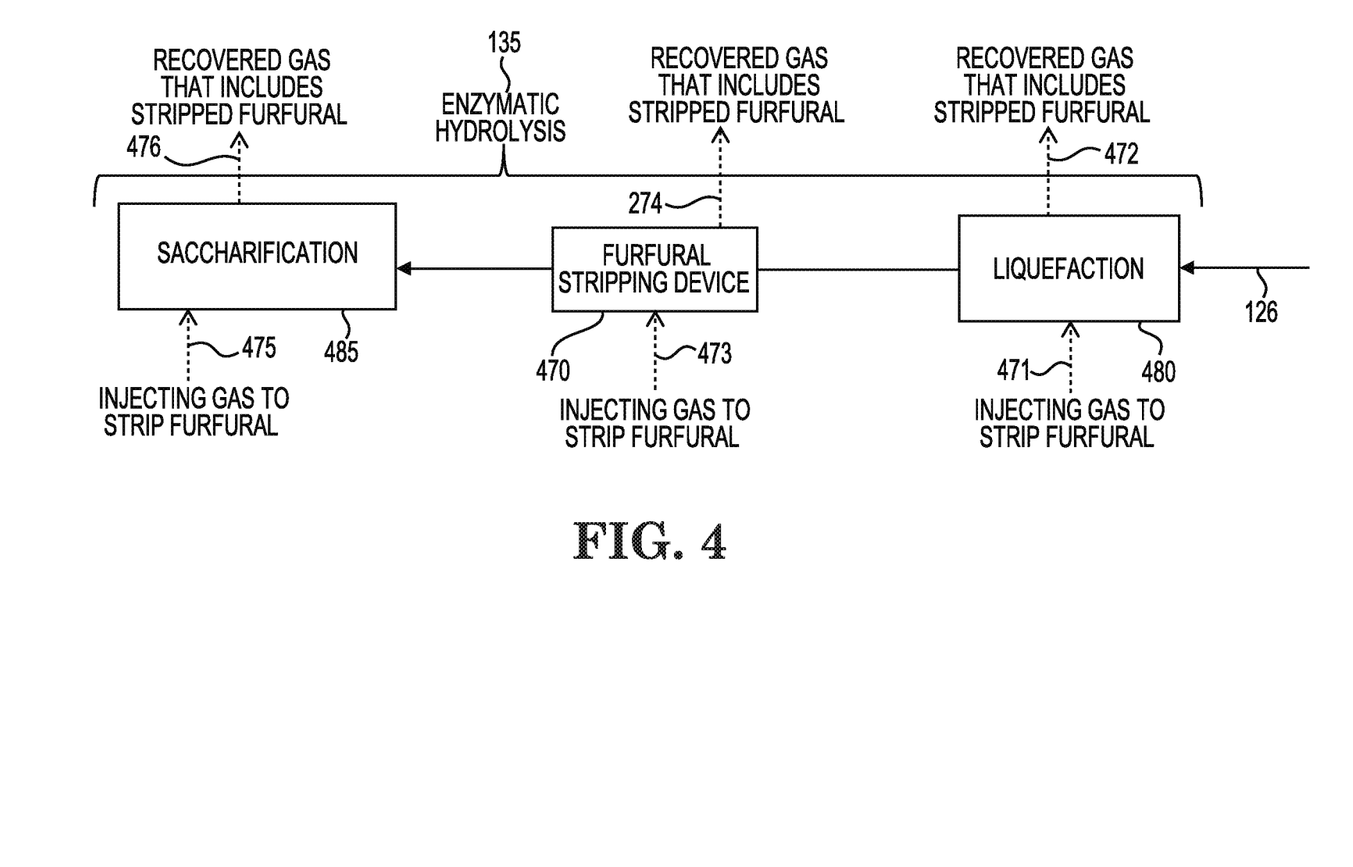
FIG. 4 shows a schematic of an exemplary enzymatic hydrolysis process that can be used in the process of FIG. 1.

In some embodiments, as shown in FIG. 4, enzymatic hydrolysis 135 can include liquefying 485 (liquefaction) at least a portion of the cellulose in the hydrolysate 125 followed by saccharifying 485 (saccharification) at least a portion of the liquefied cellulose to form glucose. Liquefaction can include adding one or more cellulase enzymes to the whole broth hydrolysate composition 125 to liquefy at least a portion of the cellulose.

A liquefaction system 480 can include one or more vessels (not shown) containing a whole broth hydrolysate and configured to maintain the whole broth hydrolysate at a pH and temperature for a time period to convert at least a portion of the cellulose in the lignocellulosic biomass into an oligosaccharide and/or a monosaccharide. In some embodiments, the temperature of the whole broth hydrolysate during at least a portion of liquefaction is in a range from 45° C. to 65° C., or even from 50° C. to 60° C. In some embodiments, the pH of the whole broth hydrolysate during at least a portion of liquefaction is in a range from 4 to 6, or even from 4.5 to 5.5. In some embodiments, the liquefaction time period is in the range from 2 to 20 hours, or even from 6 to 8 hours.

As shown, a saccharification system 485 is in fluid communication with the liquefaction system 480. In some embodiments, a saccharification system can include at least one reactor configured to receive the liquefied cellulose so as to saccharify at least a portion of the liquefied cellulose and form glucose. A saccharification system 485 can include one or more batch reactors (not shown) in fluid communication with the liquefaction system 225 to receive the liquefied cellulose. The saccharification system 485 can be configured to maintain a whole broth hydrolysate at a pH and a temperature for a time period to convert at least a portion of the cellulose in the lignocellulosic biomass into an oligosaccharide and/or a monosaccharide. In some embodiments, the temperature of the whole broth hydrolysate can be in a range from 45° C. to 65° C., or even from 50° C. to 60° C. In some embodiments, the pH of the whole broth hydrolysate can be in a range from 4 to 6, or even from 4.5 to 5.5. In some embodiments, the saccharification time period is in the range from 48 to 120 hours, or even from 112 to 114 hours.

C. Using a Hydrolysate Composition to Propagate a Microorganism

A hydrolysate composition can be used to propagate a microorganism. Propagation can be used to reproduce an initial (e.g., "starter") population of a microorganism so as to generate a larger population of the microorganism that is sufficient for use in fermentation and to make a fermentation product. For example, a first cell mass of a microorganism, a carbon source, and a nutrient source can be combined in a propagation system so that the first cell mass can reproduce and form a second cell mass (e.g., 10, 20, 50, 100, 150, or even 200 times or more greater than the first cell mass). The second cell mass can then be used in a fermentation system to convert one or more monosaccharides (e.g., from a pretreated lignocellulosic biomass) into a fermentation product that includes a biochemical such as bio-protein, bio-oil, or a biofuel (e.g., ethanol, butanol, and the like). Propagation is further described in U.S. Pat. No. 9,340,767 (Narendranath); U.S. Pat. No. 9,034,631 (Narendranath et al.); U.S. Pat. No. 8,450,094 (Narendranath et al.); and U.S. Pat. No. 9,234,167 (Narendranath et al.); U.S. Pat. No. 9,416,376 (Narendranath et al.); U.S. Pub. No. 2015-0368679-A1 (Narendranath et al.); and WO 2016/205596 (Narendranath et al.), the entirety of which patent documents are incorporated herein by reference for all purposes.

Microorganisms that can convert one or more monosaccharides into a biochemical include, e.g., algae, bacteria and/or fungi such as yeast. The product biochemicals can vary depending on the conditions that are provided. In many embodiments, the biochemicals include biofuels such as ethanol, butanol, and the like. In some embodiments, the microorganism includes one or more ethanologenic microorganisms referred to as "ethanologens". As used herein, an "ethanologen" refers to a microorganism that can convert one or more monosaccharides (e.g., glucose and the like) into at least ethanol.

Exemplary yeast and fungus include the genus of, *Aspergillus, Candida, Pichia, (Hansenula), Phanerochaete, Kloeckera (Hanseniaspora), Kluyveromyces, Rhodotorula, Torulopsis, Zygosaccharomyces, Yarrowia*, and *Saccharomyces*. In some embodiments, the yeast is a strain of *Saccharomyces cerevisiae* yeast. In some embodiments, the microorganism to be propagated includes genetically modified yeast such as genetically modified *Saccharomyces cerevisiae* that can convert glucose and xylose into a biochemical such as ethanol.

As used herein, a "carbon source" refers to one or more compounds that include at least one carbon atom and can be used by a microorganism such as yeast to grow and/or reproduce to create additional biomass. Exemplary carbon sources include monosaccharides such as glucose, fructose, galactose, mannose, xylose and the like; disaccharides such as lactose, maltose, sucrose, cellobiose and the like; oligosaccharides; polysaccharides such as cellulose, hemicelluloses, starch, xylan and the like; single carbon substrates including only one carbon atom such as methanol; and polyols such as glycerol, but not limited thereto. In some embodiments, a whole broth hydrolysate can be used as a carbon source.

In addition to a carbon source, a nutrient source is also included to help propagate microorganisms such as ethanologens. As used herein, a "nutrient source" refers to one or more materials that can be used by a microorganism to grow and/or reproduce to create additional microorganisms and is different from a carbon source. The nutrient source used can include a stillage component (e.g. whole stillage, thin stillage and/or syrup). Whole stillage is well-known and is a byproduct of distilling a fermentation product. For example, a well known process for making whole stillage is a corn grain-to-ethanol process.

Figure 9:
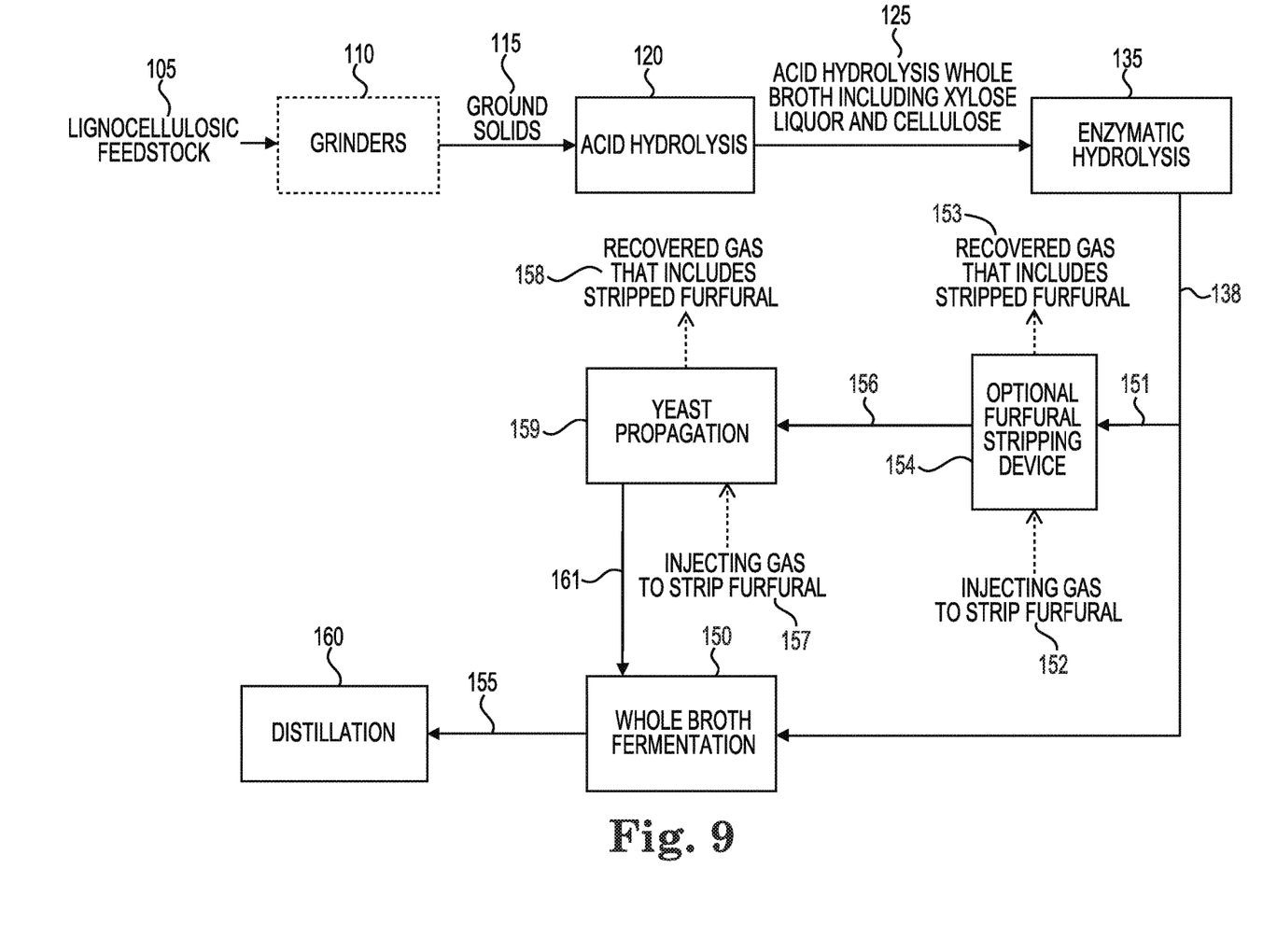
FIG. 9 shows a schematic of an exemplary process for gas stripping furfural from a whole broth hydrolysate in the context of a system 100 for making ethanol via fermentation.
Figure 10:
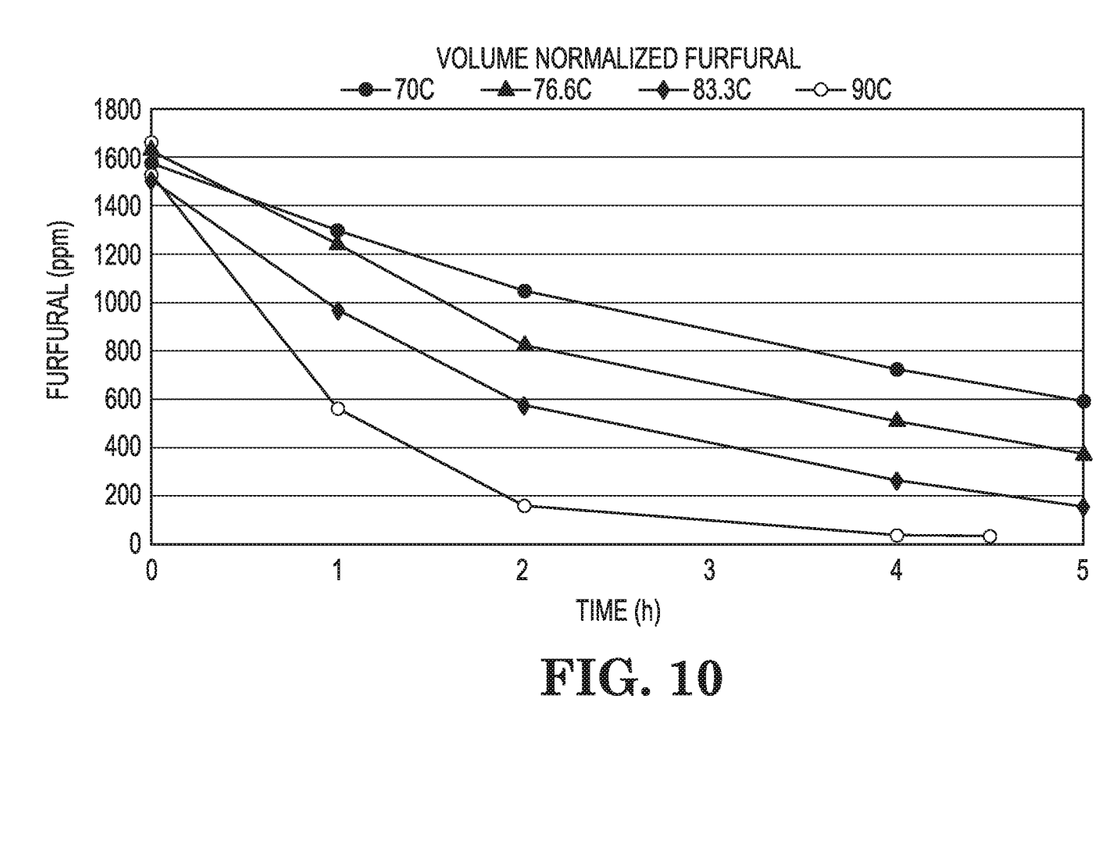
FIG. 10 shows a graph of furfural concentration concentration versus sparge time for samples at different temperatures in Example 3.

FIG. 9 shows an embodiment of using at hydrolysate composition to propagate a microorganism such as yeast. For illustration purposes, the same reference characters used in FIG. 1 are used to show like features illustrated in FIG. 9.

As shown in FIG. 9, after enzymatic hydrolysis 135 at least a portion 151 of the whole broth hydrolysate 138 from enzymatic hydrolysis 135 can be used as carbon source in a whole broth yeast propagation vessel 159 to generate a desirable yeast cell mass required for fermentation. Treating the whole broth hydrolysate prior to yeast propagation is discussed below in connection with FIG. 9.

D. Gas Stripping One or More Fermentation Inhibitors

Embodiments of the present disclosure include using a gas to remove (strip) at least a portion (e.g., substantially all) of one or more fermentation inhibitors from a hydrolysate (e.g., whole broth hydrolysate). A gas can be injected into a hydrolysate composition at one or more points in a process from acid hydrolysis through enzymatic hydrolysis, and before fermentation.

Using a gas to strip a fermentation inhibitor is described herein below with reference to FIGS. 1-10.

D.1 Inject Gas

Gas stripping can include injecting a first volume of a gas into a hydrolysate (e.g., a whole broth hydrolysate composition) to provide a treated, hydrolysate composition. The hydrolysate composition includes furfural in a first concentration and the treated, hydrolysate composition includes furfural in a second concentration. By injecting a gas into the hydrolysate composition to treat it, at least a portion of the furfural transfers into the gas from the hydrolysate composition such that the second concentration of furfural in the treated, hydrolysate composition is less than the first concentration of furfural in the untreated hydrolysate. In some embodiments, the first concentration of furfural in the hydrolysate is 500 ppm or greater, 750 ppm or greater, 1000 ppm or greater, 1200 ppm or greater, 1500 ppm or greater, or even 3000 ppm or greater. In some embodiments, the second concentration of furfural in a treated, hydrolysate composition is less than 500 ppm, less than 250 ppm, less than 100 ppm, less than 50 ppm, or even less than 1 ppm (e.g., undetectable).

A variety of types of gases can be used to strip an inhibitor such as furfural. In some embodiments, a gas can include air, oxygen, inert gas, and mixtures thereof.

The temperature and pressure of the gas/hydrolysate interface can be selected so as to facilitate transfer of a fermentation inhibitor such as furfural into the gas phase. For example, the vapor pressure of the fermentation inhibitor(s) such as furfural can be considered when determining the temperature and pressure of the hydrolysate during gas stripping. In some embodiments, it is desirable to select a temperature and pressure of the given unit operation such as acid hydrolysis, enzymatic hydrolysis, and the like. In some embodiments, a temperature can be selected specifically for gas stripping that may be different from a target temperature that is selected for a different process such as hydrolysis and/or propagation. For example, gas stripping can be performed at a temperature in the range from 20° C. to 100° C., or even 70° C. to 95° C. In some embodiments, gas stripping can be performed under vacuum, at atmospheric pressure, or a pressurized environment.

Another factor to consider can include devices or elements to facilitate mixing of a hydrolysate composition and an injected gas. See, e.g., FIGS. 5 and 6 discussed below.

A volume of gas to treat a hydrolysate composition can be selected depending on, e.g., the volume of the hydrolysate to be treated. In some embodiments, the volume of the gas is injected at a rate of at least 0.01 volume unit of gas per volume unit of hydrolysate composition per minute, at least 0.05 volume unit of gas per volume unit of hydrolysate composition per minute, at least 0.1 volume unit of gas per volume unit of hydrolysate composition per minute, at least 0.5 volume unit of gas per volume unit of hydrolysate composition per minute, at least 1.0 volume unit of gas per volume unit of hydrolysate composition per minute, or even at least 5.0 volume unit of gas per volume unit of hydrolysate composition per minute. An example of "volume unit of gas per volume unit of hydrolysate composition per minute" is "liter of gas per liter of hydrolysate composition per minute."

Figure 5:
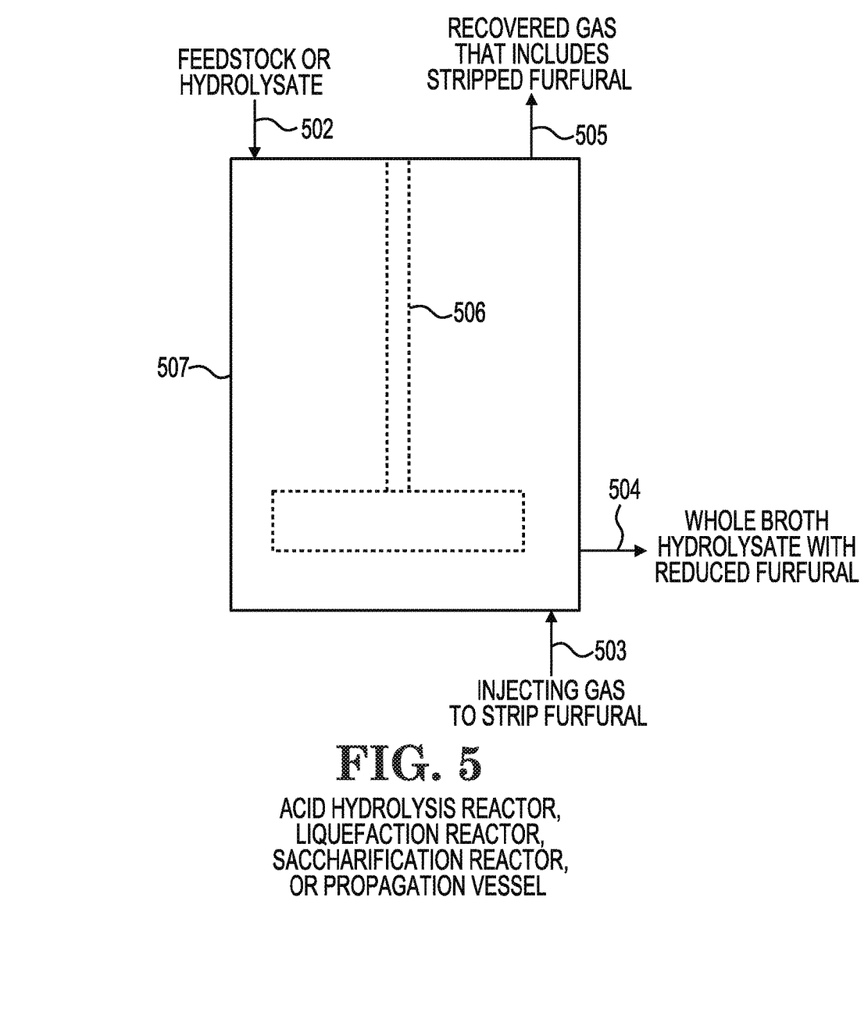
FIG. 5 shows a schematic of an exemplary enzymatic hydrolysis vessel that can be used in the process of FIG. 1.

A variety of systems and devices can be used to inject a gas into a hydrolysate composition. For example, a gas such as compressed air can be sparged into a vessel via one or more gas ports. The gas ports may positioned along one or more linear gas supply tubes or pipes positioned near the bottom of a vessel. As another example, gas ports may be positioned around a ring-shaped tube or pipe positioned near the bottom of a vessel. In some embodiments, the gas ports can be coupled to an existing vessel such as an acid hydrolysis tank, a liquefaction tank, a saccharification tank, and/or a propagation tank. For example, as shown in FIG. 5, a tank 507 used for hydrolysis (e.g., acid or enzymatic (liquefaction or saccharification)) can receive feedstock (e.g., in an acid hydrolysis tank) or a hydrolysate (e.g., in a liquefaction tank, a saccharification tank, or a propagation tank). Tank 507 also has a stirring mechanism 506 and is coupled to a source of gas 503 so that gas can be injected into the composition contained in tank 507 so that furfural can transfer from the hydrolysate composition into the gas phase. Stirring mechanism 506 can facilitate mixing of the gas and the hydrolysate composition so as to help transfer furfural from the hydrolysate composition into the gas phase. In some embodiments, a stirring mechanism can be driven at a speed to facilitate mixing of the gas and the hydrolysate composition so as to help transfer furfural from the hydrolysate composition into the gas phase. One way to determine and control the desired level of mixing is to set the mixing motor at a horsepower (hp) for a given volumetric unit of hydrolysate composition. In some embodiments, a mixing apparatus motor can be set to run at a horsepower in the range from 0.1 hp/1000 gallons of hydrolysate composition to 10 hp/1,000 gallons of hydrolysate composition, from 0.5 hp/1,000 gallons of hydrolysate composition to 5 hp/1,000 gallons of hydrolysate composition, or even from 1 hp/1,000 gallons of hydrolysate composition to 3 hp/1,000 gallons of hydrolysate composition. Accordingly, selecting a mixing motor can be performed by dividing the motor horsepower by the volume of the tank contents or by measuring the actual power draw on the motor during operation and dividing that by the volume of the tank contents.

Another way to determine and control the desired level of mixing is to set the rpms of the mixing apparatus. In some embodiments, the stirring mechanism can operate an rpm in the range from 300 rpms to 3000 rpms, or even 500 to 1500 rpms.

Figure 6:
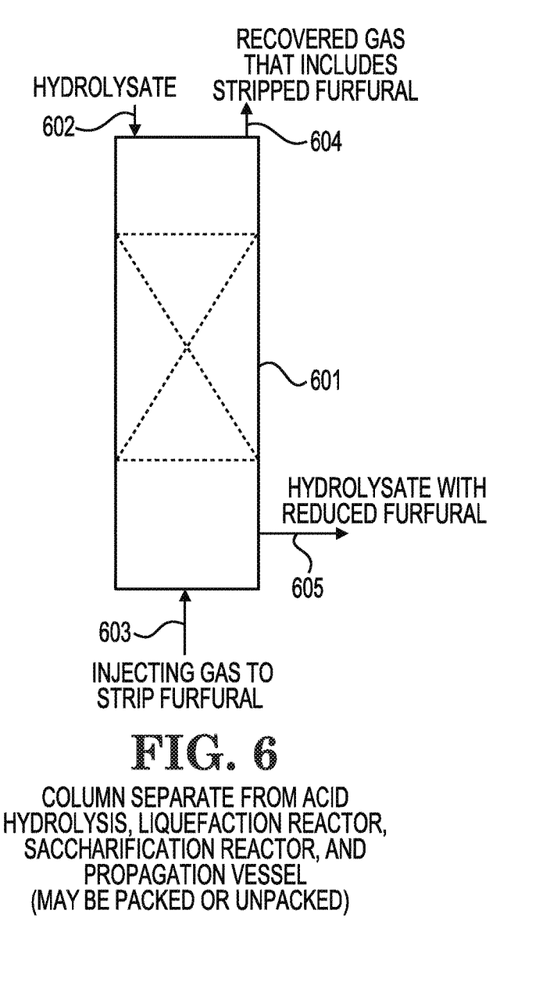
FIG. 6 shows a schematic of an exemplary, dedicated gas stripping vessel that can be used in the process of FIG. 1.

As another example, a dedicated device or tank can be used to strip a fermentation inhibitor such as furfural from a hydrolysate composition such as a whole broth hydrolysate. FIG. 6 illustrates such a device. FIG. 6 shows a column 601 that can receive a hydrolysate 602 that includes furfural. Column 601 is coupled to a source of gas 603 so that gas can be injected into the composition contained in column 601 so that furfural can transfer from the hydrolysate composition into the gas phase. If desired, column 601 can be packed so as to facilitate mixing of the gas and the hydrolysate composition to help transfer furfural from the hydrolysate composition into the gas phase.

D.2 Recovering Gas

Referring to FIG. 5, gas that includes furfural can be recovered 505 from tank 507 so that the furfural in the gas phase can be separated from the hydrolysate composition and provide a hydrolysate composition 504 with a reduced amount of furfural.

Referring to FIG. 6, gas that includes furfural can be recovered 604 from column 601 so that the furfural in the gas phase can be separated from the hydrolysate composition and provide a hydrolysate composition 605 with a reduced amount of furfural.

A gas recovery system can be in fluid communication with one or more vessels such as tank 507 and column 601. The gas recovery system can be configured to recover gas from the stripping process. Such a system can include hoods, ducts, pipes, and the like.

A gas stripping process as described herein can be implemented at one or more points in a process such as process 100 for making ethanol via fermentation. Several points are illustrated in FIGS. 1-4 and 9. It is noted that one or more of the gas stripping locations illustrated in FIGS. 1-4 and 9 can be implemented as desired. All of the gas stripping locations are shown for illustration purposes.

As shown in FIG. 1, a dedicated gas stripping device 130 can be in fluid communication with acid hydrolysis system 120 to receive a whole broth hydrolysate and inject a gas 131 into the whole broth hydrolysate contained in device 130. The injected gas can interface with the whole broth hydrolysate so that one or more fermentation inhibitors such as furfural can transfer from the whole broth hydrolysate into the gas phase. Gas including the furfural can be recovered 132 from device 130. As shown, gas stripping device is also in fluid communication with enzyme hydrolysis system 135 so that the treated, whole broth hydrolysate from device 130 can be provided to enzymatic hydrolysis 135.

FIG. 1 shows another dedicated gas stripping device 140 that is in fluid communication with enzymatic hydrolysis system 135 to receive a whole broth hydrolysate and inject a gas 141 into the whole broth hydrolysate contained in device 140. The injected gas can interface with the whole broth hydrolysate so that one or more fermentation inhibitors such as furfural can transfer from the whole broth hydrolysate into the gas phase. Gas including the furfural can be recovered 142 from device 140. As shown, gas stripping device 140 is also in fluid communication with whole broth fermentation 150 so that the treated, whole broth hydrolysate from device 140 can be provided to whole broth fermentation 150.

FIG. 1 also shows that enzymatic hydrolysis system 135 is configured to inject a gas 136 into the whole broth hydrolysate contained in the enzymatic hydrolysis system 135. The injected gas can interface with the whole broth hydrolysate contained in the enzymatic hydrolysis system 135 so that one or more fermentation inhibitors such as furfural can transfer from the whole broth hydrolysate into the gas phase. Gas including the furfural can be recovered 137 from the enzymatic hydrolysis system 135. If desired, gas stripping device 140 can be eliminated so that the treated, whole broth hydrolysate from the enzymatic hydrolysis system 135 can be provided directly to whole broth fermentation 150.

As shown in FIG. 2, if desired, another dedicated gas stripping device 292 can be included that is in fluid communication with enzymatic hydrolysis system 135 to receive a whole broth hydrolysate from the steam explosion system 295 and inject a gas 293 into the whole broth hydrolysate contained in device 292. The injected gas can interface with the whole broth hydrolysate so that one or more fermentation inhibitors such as furfural can transfer from the whole broth hydrolysate into the gas phase. Gas including the furfural can be recovered 294 from device 292. As shown, gas stripping device 292 is also in fluid communication with enzymatic hydrolysis system 135 so that the treated, whole broth hydrolysate from device 292 can be provided to enzymatic hydrolysis system 135.

As shown in FIG. 3, if desired, another dedicated gas stripping device 392 can be included that is in fluid communication with acid hydrolysis system 120 to receive a xylose liquor from the acid hydrolysis system 120 and inject a gas 393 into the xylose liquor contained in device 392. The injected gas can interface with the xylose liquor so that one or more fermentation inhibitors such as furfural can transfer from the xylose liquor into the gas phase. Gas including the furfural can be recovered 394 from device 392. As shown, gas stripping device 392 is also in fluid communication with enzymatic hydrolysis system 135 so that the treated, xylose liquor from device 392 can be provided to enzymatic hydrolysis system 135.

As shown in FIG. 4, if desired, another dedicated gas stripping device 470 can be included that is in fluid communication with liquefaction system 480 to receive a whole broth hydrolysate from the liquefaction system 480 and inject a gas 473 into the whole broth hydrolysate contained in device 470. The injected gas can interface with the whole broth hydrolysate so that one or more fermentation inhibitors such as furfural can transfer from the whole broth hydrolysate into the gas phase. Gas including the furfural can be recovered 273 from device 470. As shown, gas stripping device 470 is also in fluid communication with saccharification system 485 so that the treated, whole broth hydrolysate from device 470 can be provided to saccharification system 485.

FIG. 4 also shows that liquefaction system 480 is configured to inject a gas 471 into the whole broth hydrolysate contained in the liquefaction system 480. The injected gas can interface with the whole broth hydrolysate contained in the liquefaction system 480 so that one or more fermentation inhibitors such as furfural can transfer from the whole broth hydrolysate into the gas phase. Gas including the furfural can be recovered 472 from the liquefaction system 480. If desired, gas stripping device 470 can be eliminated so that the treated, whole broth hydrolysate from the liquefaction system 480 can be provided directly to saccharification system 485.

FIG. 4 also shows that saccharification system 485 is configured to inject a gas 485 into the whole broth hydrolysate contained in the saccharification system 485. The injected gas can interface with the whole broth hydrolysate contained in the saccharification system 485 so that one or more fermentation inhibitors such as furfural can transfer from the whole broth hydrolysate into the gas phase. Gas including the furfural can be recovered 476 from the saccharification system 485. As mentioned, the gas stripping locations described herein are for illustration purposes. Accordingly, gas stripping in saccharification system 485 can be implemented instead of or in addition to gas stripping in device 470 and/or liquefaction system 480.

With respect to FIG. 9, one or more fermentation inhibitors can be stripped in gas stripping device 154 and/or yeast propagation system 159.

As shown in FIG. 9, if desired, another dedicated gas stripping device 154 can be included that is in fluid communication with enzymatic hydrolysis system 135 to receive at least a portion of whole broth hydrolysate 151 from the enzymatic hydrolysis system 135 and inject a gas 152 into the whole broth hydrolysate contained in device 154. The injected gas can interface with the whole broth hydrolysate so that one or more fermentation inhibitors such as furfural can transfer from the whole broth hydrolysate into the gas phase. For example, the gas may be introduced into device 154 in a manner to counter-currently contact the whole broth hydrolysate prior to the whole broth hydrolysate being added to the yeast propagation system 159. Gas including inhibitor such as furfural can be recovered 153 from device 154. As shown, gas stripping device 154 is also in fluid communication with yeast propagation system 159 so that the treated, whole broth hydrolysate 156 from device 154 can be provided to yeast propagation system 159.

FIG. 9 also shows that yeast propagation system 159 is configured to inject a gas 157 into the whole broth hydrolysate contained in the yeast propagation system 159. The injected gas can interface with the whole broth hydrolysate contained in the yeast propagation system 159 so that one or more fermentation inhibitors such as furfural can transfer from the whole broth hydrolysate into the gas phase. Gas including the furfural can be recovered 158 from the yeast propagation system 159.

In some embodiments, the whole broth hydrolysate can be heated in a dedicated gas stripping device as described herein (e.g., device 154) and/or in an existing vessel dedicated to another primary purpose (e.g., yeast propagation system 159) to an elevated temperature that facilitates the faster removal of a fermentation inhibitor such as furfural.

In some embodiments, a mixer such as stirring mechanism 506 may be used to facilitate the mass transfer of a fermentation inhibitor from the whole broth hydrolysate into the stripping gas.

An exemplary embodiment is described where yeast propagation system 159 includes a tank similar to tank 507. Tank 507 can be at least partially filled with whole broth hydrolysate from enzymatic hydrolysis 135. Optionally, the whole broth hydrolysate present in tank 507 can be heated to a temperature in the range from 20° C. to 100° C. Gas can be injected as described herein for a time period to strip furfural from the whole broth hydrolysate. In this embodiment, the stripping process may be operated in batch mode (e.g., 1-5 hours) until the furfural concentration has been reduced to an acceptable level. After gas stripping, the temperature of the tank 507 contents can be lowered if desired for fermentation. One or more additional propagation components can be combined with the treated whole broth hydrolysate so as to perform yeast propagation. For example, while using the whole broth hydrolysate as a carbon source, a nutrient source (e.g., thin stillage from corn ethanol production) and yeast source can be added to the treated whole broth stillage. The balance of the tank 507 volume can be filled with water.

It can be particularly advantageous to remove at least a portion (e.g., substantially all) of the furfural and/or other fermentation inhibitors from the material used to generate the desired yeast cell mass in order to provide good yeast growth that will facilitate subsequent fermentation. By having good yeast growth in yeast propagation, desirable fermentation performance can be realized in the subsequent whole broth fermentation step even in the presence of moderate levels of furfural in fermentation.

The recovered gas streams described herein that include furfural can be treated as described in section D.3.

D.3 Treating Gas to Remove Fermentation Inhibitor

The gas streams recovered from gas stripping operations described herein include fermentation inhibitors such as furfural. Such gas streams can be treated to recover furfural as a byproduct for subsequent use or sale, or can be treated to remove at least a portion of the furfural from the gas stream and dispose of it. In some embodiments, treating a recovered gas stream to remove the furfural include gas scrubbing, distillation, and the like. For example, a recovered gas stream can be cooled to condense and recover at least a portion of one or more of furfural and moisture as liquids. After condensing, the gas stream may still contain some furfural, albeit in a relatively small amount. The gas stream can be recycled and used to strip additional furfural from a hydrolysate composition. In some embodiments, the recovered gas can include air such that the recovered gas can be used as combustion air (e.g., in a boiler system) so that the furfural is degraded to a product of combustion.

E. Downstream Processes

As shown in FIG. 1, after enzymatic hydrolysis in system 135, stream 145 can be fed into fermentation system 150 so that yeast can convert xylose and glucose into ethanol. As shown in FIG. 9, after propagation in system 159, stream 161 can be fed into fermentation system 150 so that yeast can convert xylose and glucose into ethanol. The beer 155 from fermentation system 150 can be fed to distillation system 160 to recover a biochemical such as ethanol.

F. EXAMPLES

Example 1—Furfural Stripping Enzymatically Saccharified Broth

Figure 7:
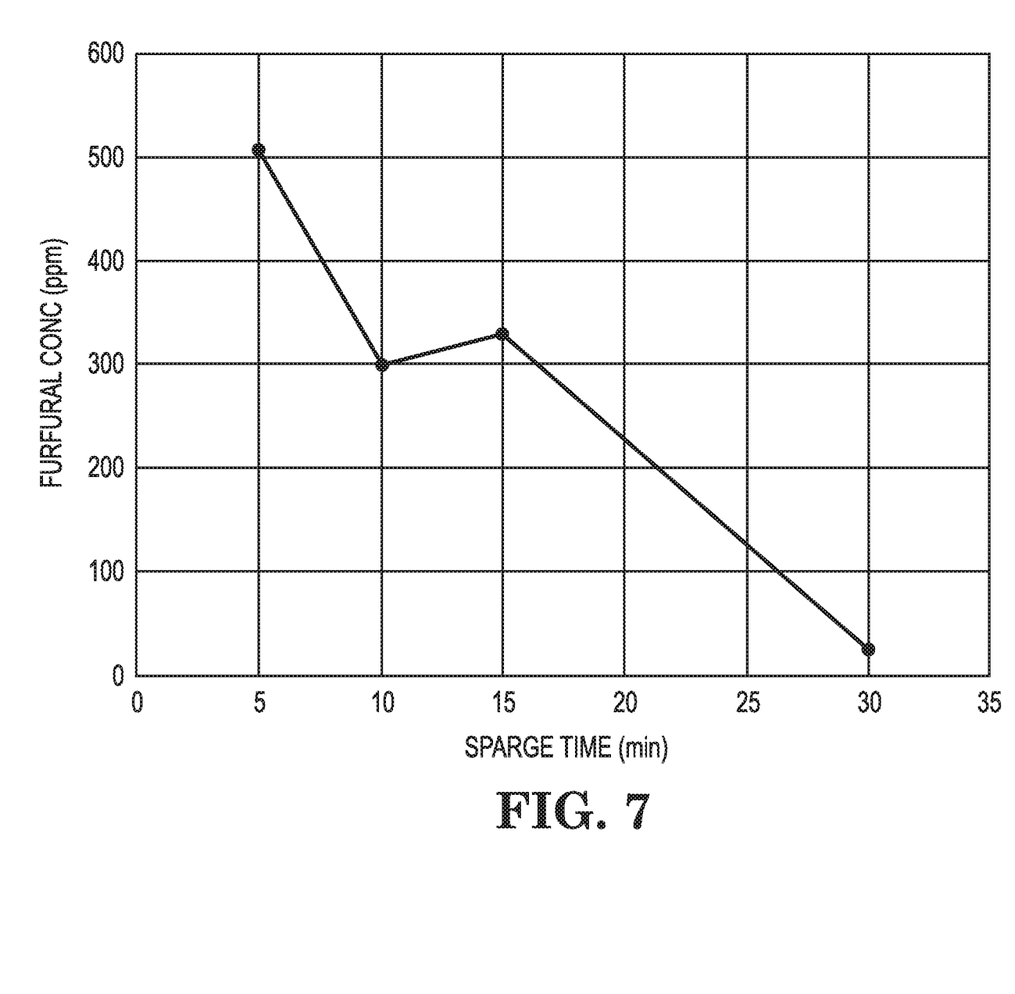
FIG. 7 shows a graph of furfural concentration versus time in Example 1.

This experiment simulated a dedicated furfural stripping device such as device 140 in FIG. 1. A Parr 4560 stainless steel pressure vessel was fitted with a dip tube with a stainless steel frit at the end. Enzymatically saccharified corn stover was loaded as-is in the reactor vessels at a volume of 70 ml. A gas cylinder was fit to the reactor through a gas hose fixed to a port on the reactor head. Nitrogen was sparged through the dip tube inlet valve. The gas was vented through one of the outlet vales in the reactor head. Temperature of the reactor contents was held at 50° C. Impellor speed was set at 800 rpm (about 50% of the impellor motor's output). Gas was sparged through at an unknown rate. Samples were sparged and the reactor vessel was taken down after reaching the end of each time point. The reactor vessels were sampled and filtered through a 0.2 µm syringe filter. The filtrate was loaded into HPLC vials and analyzed for furfural and HMF concentrations via HPLC analysis. The furfural concentration in the hydrolysate versus sparge time is shown in FIG. 7.

Example 2—Furfural Stripping During Enzymatic Saccharification

Figure 8:
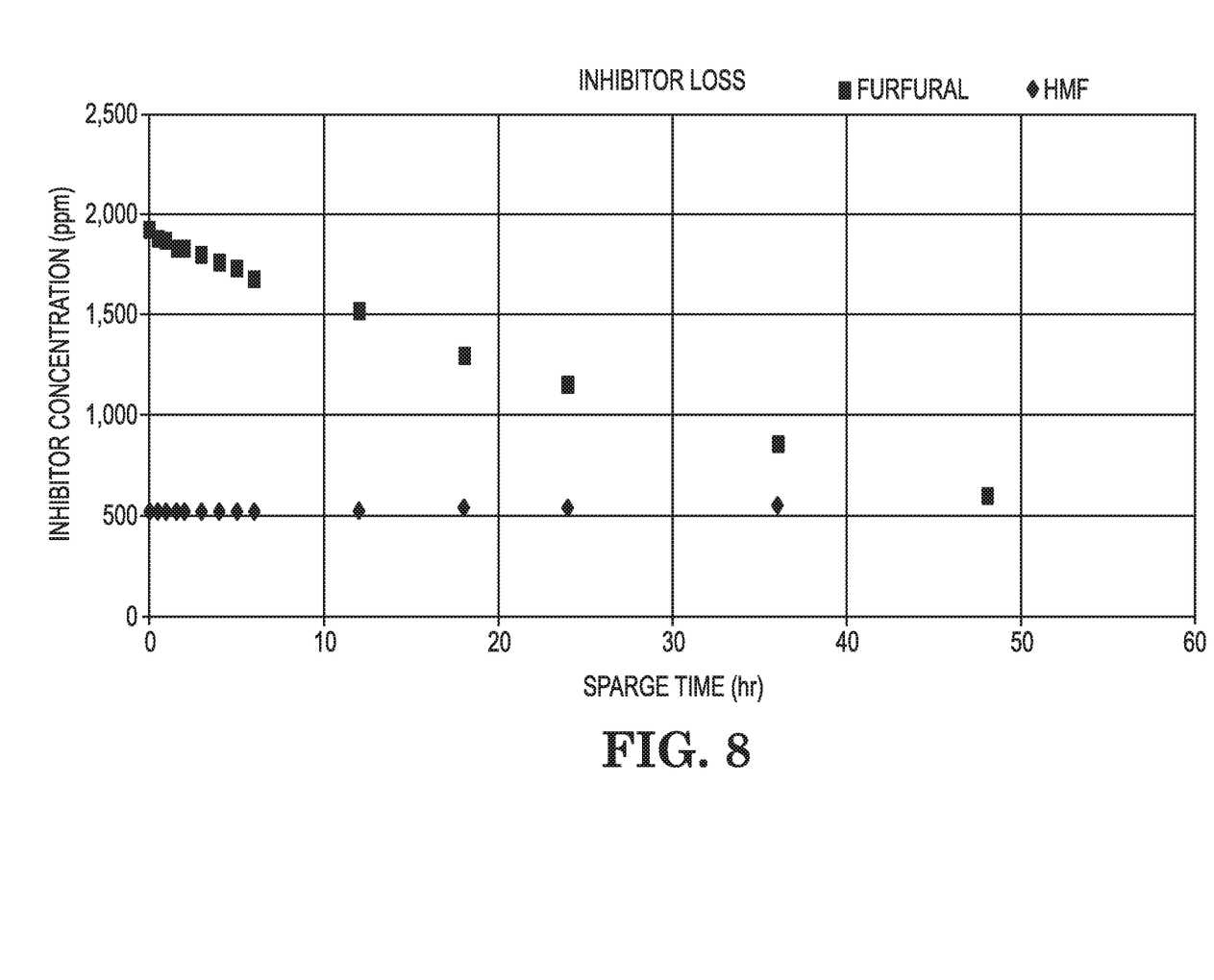
FIG. 8 shows a graph of furfural concentration and HMF concentration versus time in Example 2.

This experiment simulated stripping furfural during enzymatic saccharification in a sachharification reactor such as 485 in FIG. 4. A 3 L glass jacketed bioreactor was loaded with dilute acid pretreated corn stover. The total solids loading of the reactor was 17% and 1.5 L of slurry was used. The slurry was pH adjusted to 5 using either 30% $NH_4OH$ or 10% $H_2SO_4$ and the temperature was set to 55° C. After pH adjustment, enzyme was added to the reactor. Temperature was kept constant by circulating water through the vessel's jacket. The bioreactor was fitted with a large ribbon impellor and a smaller impellor to thoroughly mix the biomass at 350 rpm. A dip tube with small diffusing holes at the end was fixed to the head of the reactor and lowered into the biomass. Compressed air was sparged through the dip tube so that it bubbled through the biomass. The sparged gas was allowed to vent through a condenser kept at atmospheric pressure. Air was sparged at 0.1, 0.5, and 1 L/L/min. Samples were taken by removing about 1.5 ml of slurry and filtering through a 0.2 µm syringe filter. The filtrate was loaded into HPLC vials and analyzed for furfural and HMF concentrations via HPLC analysis. Samples were taken at regular intervals throughout the saccharification. The reaction was allowed to be carried out for at least 48 h. The HMF and furfural concentrations in the hydrolysate versus sparge time are shown in FIG. 8.

Example 3—Furfural Stripping Enzymatically Saccharified Broth Prior to Yeast Propagation at Different Temperatures This experiment simulated stripping furfural from a yeast propagation tank similar to the tank 507 in FIG. 5, and tank 159 in FIG. 9. Four 6.6 L Bioflo 310 tanks were filled to 25% level with enzymatically saccharified broth. The Bioflo tanks were mixed at 600 RPM and heated to the following temperatures: 70° C., 76.6° C., 83.3° C., and 90° C. Once heated, compressed air was sparged in at 2 SLPM and vented to lab ventilation. Aeration continued for up to 5 h. Samples were taken using a bulb pipette and filtered through a 0.2 µm syringe filter into HPLC vials. The samples were run using two different HPLC methods to primarily measure furfural and glucose. The furfural concentrations were normalized to the initial fill volume by multiplying the furfural concentration by the initial glucose concentration and dividing by the sample glucose concentration to correct for any water loss. Furfural concentrations based on the initial fill volume over time can be seen in FIG. 10.

What is claimed is:

1. A method of removing at least a portion of furfural from a hydrolysate composition, wherein the method comprises:
   a) providing a whole broth hydrolysate composition, wherein the providing comprises:
      i) providing lignocellulosic biomass comprising hemicellulose, cellulose, and lignin;
      ii) contacting the lignocellulosic biomass with an aqueous composition to hydrolyze at least a portion of the hemicellulose into one or more oligosaccharides and/or one or more pentoses, and form a first whole broth hydrolysate composition comprising at least pentose, cellulose, lignin, and furfural; and
      iii) enzymatically hydrolyzing at least a portion of the cellulose in the first whole broth hydrolysate composition to form a second whole broth hydrolysate composition comprising at least pentose, hexose, lignin, and furfural, wherein the furfural is present in the second whole broth hydrolysate in a first concentration;
   b) separating a first portion of the second whole broth hydrolysate composition and a second portion of the second whole broth hydrolysate composition from the second whole broth hydrolysate composition;
   c) injecting a first volume of a gas into the first portion of the second whole broth hydrolysate composition to provide a treated, whole broth hydrolysate composition, wherein the treated, whole broth hydrolysate composition comprises furfural in a second concentration, wherein the second concentration is less than the first concentration;
d) recovering a second volume of the gas from the treated, whole broth hydrolysate composition, wherein the second volume of the gas comprises furfural;
e) adding a first cell mass of yeast to the treated, whole broth hydrolysate composition;
f) propagating the first cell mass of yeast in the treated, whole broth hydrolysate composition to form a second cell mass of yeast;
g) adding the treated, whole broth hydrolysate composition, including the second cell mass of yeast, to the second portion of the second whole broth hydrolysate composition; and
h) after "g", fermenting the treated, whole broth hydrolysate composition, including the second cell mass of yeast, and the second portion of the second whole broth hydrolysate composition.

2. The method of claim 1, wherein the first concentration of furfural is 500 ppm or greater and the second concentration of furfural is less than 500 ppm.

3. The method of claim 1, wherein the first concentration is from 500 to 3000 ppm.

4. The method of claim 1, wherein the gas comprises a gas chosen from air, oxygen, inert gas, and mixtures thereof.

5. The method of claim 1, wherein the first volume of gas injected into the first portion of the second whole broth hydrolysate composition comprises no furfural.

6. The method of claim 1, further comprising treating the second volume of the gas to remove at least a portion of the furfural.

7. The method of claim 6, wherein the furfural is removed from the second volume of the gas via a scrubbing process.

8. The method of claim 1, wherein contacting the lignocellulosic biomass with an aqueous composition comprises contacting the lignocellulosic biomass with an aqueous composition comprising sulfuric acid for a time period to form the one or more pentoses and the furfural, wherein the sulfuric acid is present in an concentration in the range from 0.2 to 1.3% w/w, wherein the aqueous composition is at a temperature in the range from greater than 100° C. to 170° C., wherein the time period is a range from 15 minutes to 5 hours.

9. The method of claim 1, wherein the first portion of the second whole broth hydrolysate composition is at a temperature in the range from 20° C. to 100° C. during at least a portion of injecting the first volume of a gas into the first portion of the second whole broth hydrolysate composition.

10. The method of claim 1 wherein the second cell mass of yeast is at least 10 times greater than the first cell mass of yeast.

11. The method of claim 1, wherein enzymatically hydrolyzing at least a portion of the cellulose in the first whole broth hydrolysate composition comprises:
a) liquefying at least a portion of the cellulose, wherein liquefying comprises adding one or more cellulase enzymes to the first whole hydrolysate composition to liquefy at least a portion of the cellulose; and
b) after liquefying at least a portion of the cellulose, saccharifying at least a portion of the liquefied cellulose to form glucose.

12. The method of claim 9, wherein the first portion of the second whole broth hydrolysate composition is at a temperature in the range from 70° C. to 95° C. during at least a portion of injecting the first volume of a gas into the first portion of the second whole broth hydrolysate composition.

13. The method of claim 1, further comprising heating the first portion of the second whole broth hydrolysate composition so that the first portion of the second whole broth hydrolysate composition is at a temperature in the range from 70° C. to 95° C. during at least a portion of injecting the first volume of a gas into the first portion of the second whole broth hydrolysate composition.

14. The method of claim 1, wherein the first portion of the second whole broth hydrolysate composition is present in a propagation vessel while injecting the first volume of the gas into the first portion of the second whole broth hydrolysate composition to provide the treated, whole broth hydrolysate composition.

* * * * *